United States Patent
Heath

(10) Patent No.: US 6,878,730 B2
(45) Date of Patent: Apr. 12, 2005

(54) QUATERNARY AMMONIUM COMPOUNDS

(75) Inventor: Timothy Gordon Heath, Wildwood, MO (US)

(73) Assignee: Pharmacia & UpJohn, Kalamazoo, MI (US)

( * ) Notice: Subject to any disclaimer, the term of this patent is extended or adjusted under 35 U.S.C. 154(b) by 0 days.

(21) Appl. No.: 10/688,348

(22) Filed: Oct. 17, 2003

(65) Prior Publication Data

US 2004/0132774 A1 Jul. 8, 2004

Related U.S. Application Data

(60) Provisional application No. 60/421,962, filed on Oct. 29, 2002.

(51) Int. Cl.[7] .................... A61K 31/445; C07D 211/92; C07D 211/98
(52) U.S. Cl. ........................................ 514/358; 546/347
(58) Field of Search ........................... 546/347; 514/358

(56) References Cited

U.S. PATENT DOCUMENTS

| 3,505,337 | A | | 4/1970 | Zeile et al. ................. 260/292 |
|---|---|---|---|---|
| 5,036,098 | A | | 7/1991 | Kimura et al. ............... 514/438 |
| 5,948,792 | A | * | 9/1999 | Tsuchiya et al. ............ 514/317 |
| 6,040,449 | A | * | 3/2000 | Tsuchiya et al. ............ 546/193 |
| 6,130,232 | A | * | 10/2000 | Mase et al. .................. 514/318 |
| 6,469,172 | B2 | * | 10/2002 | Maligres et al. ............ 546/193 |
| 2001/0051727 | A1 | | 12/2001 | Maligres et al. ............ 546/193 |

FOREIGN PATENT DOCUMENTS

DE    0106643    6/1974    ........... C07D/29/24

OTHER PUBLICATIONS

Int. J. Pharm, 33, 201–217, 1986.

* cited by examiner

Primary Examiner—Rita Desai
(74) Attorney, Agent, or Firm—Peter C. Richardson; Gregg C. Benson; Robert T. Ronau

(57) ABSTRACT

The invention features quaternary ammonium compounds of formula I, described herein, and their use in treating asthma, chronic obstructive pulmonary disorder, allergic rhinitis, and infectious rhinitis.

10 Claims, No Drawings

QUATERNARY AMMONIUM COMPOUNDS

CROSS REFERENCE TO RELATED APPLICATIONS

This application claims the benefit of U.S. Provisional Application Ser. No., 60/421,962, filed Oct. 29, 2002, which is incorporated herein by reference in its entirety.

TECHNICAL FIELD

The present invention concerns a novel class of quaternary ammonium compounds, pharmaceutical compositions containing the same, the compounds for use as medicaments, and use of the compounds for the manufacture of specific medicaments. The present invention also concerns a method of treatment involving administration of the compounds. The novel compounds are useful as antimuscarinic agents. In particular, the novel compounds are useful for the treatment of asthma, a group of breathing disorders termed Chronic Obstructive Pulmonary Disease (COPD), allergic rhinitis, and infectious rhinitis.

BACKGROUND OF THE INVENTION

"Asthma" refers to a chronic lung disease causing bronchoconstriction (narrowing of the airways) due to inflammation (swelling) and tightening of the muscles around the airways. The inflammation also causes an increase in mucus production, which causes coughing that may continue for extended periods. Asthma is generally characterized by recurrent episodes of breathlessness, wheezing, coughing, and chest tightness, termed exacerbations. The severity of exacerbations can range from mild to life threatening. The exacerbations can be a result of exposure to e.g. respiratory infections, dust, mold, pollen, cold air, exercise, stress, tobacco smoke, and air pollutants.

"COPD" refers to Chronic Obstructive Pulmonary Disease, primarily associated with past and present cigarette smoking. It involves airflow obstruction, mainly associated with emphysema and chronic bronchitis. Emphysema causes irreversible lung damage by weakening and breaking the air sacs within the lungs. Chronic Bronchitis is an inflammatory disease, which increases mucus in the airways and bacterial infections in the bronchial tubes, resulting in obstructed airflow.

"Allergic rhinitis" refers to acute rhinitis or nasal rhinitis, including hay fever. It is caused by allergens such as pollen or dust. It may produce sneezing, congestion, runny nose, and itchiness in the nose, throat, eyes, and ears.

"Infectious rhinitis" refers to acute rhinitis or nasal rhinitis of infectious origin. It is caused by upper respiratory tract infection by infectious rhinoviruses, coronaviruses, influenza viruses, parainfluenza viruses, respiratory syncytial virus, adenoviruses, coxsackieviruses, echoviruses, or Group A beta-hemolytic Streptococci and generically referred to as the common cold. It may produce sneezing, congestion, runny nose, and itchiness in the nose, throat, eyes, and ears.

SUMMARY OF THE INVENTION

In one aspect, the invention features quaternary ammonium compounds of formula I

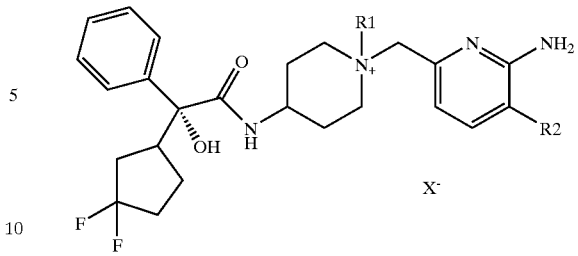

and any stereoisomers thereof, wherein $R_1$ is selected from $C_1$–$C_6$ alkyl, —$CH_2$—($C_1$–$C_4$ alkenyl), and —$CH_2$—($C_1$–$C_6$ alkynyl), each of which is optionally substituted with a group selected from phenyl, $C_1$–$C_4$ alkoxy, and hydroxyl;

$R_2$ is selected from H or OH; and

X represents an anion of a pharmaceutically acceptable acid.

Embodiments of this aspect of the invention may include one or more of the following. X is selected from the group consisting of the anions of the following acids: tartaric, hydrochloric, hydrobromic, hydroiodic, sulfuric, phosphoric, nitric, citric, methanesulfonic, $CH_3$—$(CH_2)_n$—COOH where n is 0–4, HOOC—$(CH_2)_n$—COOH where n is 1–4, HOOC—CH=CH—COOH, and benzoic. X is selected from the group consisting of iodide, bromide, and chloride. The compound is (2R)-N-[1-(6-aminopyridin-2-ylmethyl)1-methylpiperdin-4-yl]-2-[(1R)-3,3,-difluorocyclopentyl]-2-hydroxy-2-phenylacetamide iodide or (2R)-N-[1-(6-amino-5-hydroxypyridin-2-ylmethyl)1-methylpiperdin-4-yl]-2-[(1R)-3,3,-difluorocyclopentyl]-2-hydroxy-2-phenylacetamide iodide.

In another aspect the invention features a pharmaceutical composition including a therapeutically effective amount of a quaternary ammonium compound of formula I. The pharmaceutical composition may include a suitable pharmaceutical carrier.

In another aspect the present invention also provides a quaternary ammonium compound of formula I for use as a medicament. The present invention also includes using a quaternary ammonium compound of formula I for the manufacture of a medicament for treating asthma, chronic obstructive pulmonary disease (COPD), allergic rhinitis, and infectious rhinitis.

In yet another aspect, the invention provides a method of treating asthma, chronic obstructive pulmonary disease (COPD), allergic rhinitis, or infectious rhinitis in a mammal, including man, comprising administering to said mammal, in need of such a treatment, a therapeutically effective amount of a quaternary ammonium compound of formula I.

Advantageously, the quaternary ammonium compounds of formula I unexpectedly exhibit prolonged efficacy as an antimuscarininc agent when compared to tertiary amine, e.g., non-quaternized, forms of the compounds.

DESCRIPTION OF THE INVENTION

In describing the preferred embodiment, certain terminology will be utilized for the sake of clarity. Such terminology is intended to encompass the recited embodiments, as well as all technical equivalents that operate in a similar manner for a similar purpose to achieve a similar result. To the extent that any pharmaceutically active compound is disclosed or claimed, it is expressly intended to include all active metabolites produced in vivo, and, is expressly intended to include all enantiomers, isomers or tautomers where the compound is capable of being present in its enantiomeric, isomeric or tautomeric form. All stereoisomers have useful activity. Therefore, the invention includes use of each stereoisomer separately, as well as mixtures thereof.

The compounds of formula I can be prepared by one skilled in the art. The quaternary ammonium compounds of formula I may be prepared by means, well known to those skilled in the art, for preparing quaternary ammonium compounds from tertiary amines. For instance, the quaternary ammonium compounds may be produced by alkylating the piperdinyl tertiary nitrogen using the tertiary amines of U.S. Patent Application No. 2001/0051727A1, the contents of which are hereby incorporated by reference, and other known compounds as starting materials.

The general term "quaternary ammonium compound" relates to any compound that can be regarded as derived from ammonium hydroxide or an ammonium salt by replacement of all four hydrogen atoms of the $NH_4$-ion by organic groups. The specific compounds are for nomenclature reasons (see e.g. Chemical Abstracts) named as "aminium" compounds, but it is possible to use the term "ammonium" in the names. For example, (3R)-3-(2-hydroxy-s-methylphenyl)-N,N-diisopropyl-N-methy-3-phenylpropanyl-aminium bromide can also be named as an ammonium compound: (3R)-[3-(2-hydroxy-s-methylphenyl)-3-phenylpropyl] diisopropylmethylammonium bromide.

By way of example, a tertiary amine according to U.S. Patent Application No. 2001/0051727A1, or its salt, is dissolved in a suitable solvent. The tertiary amine is allowed to react with an organic substrate, e.g. an organic halide. The substrate contains a $C_1$–$C_6$ alkyl, preferably a $C_1$–$C_3$ alkyl, optionally substituted with phenyl, and a leaving group. The identity of the leaving group is not critical, but it is preferred that the leaving group is a halide, such as iodide or bromide. Thus, exemplary substrates include methyl iodide, methyl bromide, ethyl iodide, propyl iodide, benzyl bromide or benzyl iodide. The resulting reaction product is a quaternary ammonium compound, which is readily crystallized in suitable solvents, known to those skilled in the art. The crystals thus produced are quaternary ammonium salts. Their identity is confirmed by standard methods, such as melting point determination, nuclear magnetic resonance (NMR) analysis and mass spectrometry.

The compounds of the invention are preferably administered as quaternary ammonium salts which include counter ions. X represents the anion, e.g., the counter ion, of a pharmaceutically acceptable acid. For instance X may be selected from the following anions: tartrate, chloride, bromide, iodide, sulfate, phosphate(s), nitrate, citrate, methanesulfonate, carboxylates with from two to six carbon atoms, dicarboxylates with from two to six carbon atoms, maleate, fumarate, and benzoate. For other acceptable quaternary ammonium salts, see Int. J. Pharm., 33, 201–217 (1986). Particularly preferred ions are chloride, iodide and bromide, especially bromide and iodide.

The substituent $R_1$ is selected from the group including $C_1$–$C_6$ alkyl, straight or branched, optionally substituted with 1–2 of phenyl or hydroxyl, or both. Thus, $R_1$ independently represent methyl, ethyl, propyl, isopropyl, butyl, isobutyl, pentyl, isopentyl, hexyl, or isohexyl, optionally substituted with 1–2 of phenyl or hydroxyl, or both. It is particularly preferred that $R_1$ represents methyl or ethyl, preferably methyl.

The compounds according to the present invention are antimuscarinic agents. "Antimuscarinic agents" refer to muscarinic receptor antagonists. Examples of known antimuscarinic agents include tolterodine, hydroxytolterodine, 2-(diisopropylamino) ethyl-1-phenylcyclopentanecarboxylate, propiverine, oxybutynin, trospium, temiverine, and ipratropium.

Propiverine is 1-methyl-4-piperidyl α,α-diphenyl-α-(n-propoxy)acetate and is disclosed in East German Patent 106,643 and in CAS 82-155841s (1975). Trospium is 3α-hydroxyspiro [1αH,5αH-nortropane 8,1'pyrrolidinium] chloride benzilate. Temiverine is 3S benzeneacetic acid, α-cyclohexyl-α-hydroxy-,4-(diethylamino)-1,1-dimethyl-2-butynyl ester and is disclosed in U.S. Pat. No. 5,036,098. Ipratropium is 8-isopropylnoratropine methobromide and is disclosed in U.S. Pat. No. 3,505,337.

The compounds of formula I have anti-cholinergic properties and unexpectedly exhibit prolonged activity in the lung. Thus, the compounds of formula I are useful for the treatment of acetylcholine-mediated disorders. In particular, the compounds of are useful for treating asthma, chronic obstructive pulmonary disease (COPD), allergic rhinitis, and infectious rhinitis.

The compounds of the present invention are used to treat mammals, including man and horse. It is preferred that the mammal is a human. The compounds according to the invention, in the form of free base or salts with pharmaceutically acceptable acids, or solutions thereof, can be brought into suitable dosage forms, such as compositions for administration through the oral, rectal, transdermal, parenteral, nasal, or pulmonary route in accordance with accepted pharmaceutical procedures. In particular, the compositions may be administered via inhalation or insufflation. Such pharmaceutical compositions according to the invention comprise the compounds according to the invention in association with compatible pharmaceutically acceptable carrier materials, or diluents, as is well known in the art. The carriers may be any inert material, organic or inorganic, suitable for administration, such as: water, gelatin, gum arabicum, lactose, microcrystalline cellulose, starch, sodium starch glycolate, calcium hydrogen phosphate, magnesium stearate, talcum, colloidal silicon dioxide, and the like. Such compositions may also contain other pharmaceutically active agents, and conventional additives such as stabilizers, wetting agents, emulsifiers, flavoring agents, buffers, binders, disintegrants, lubricants, glidants, antiadherents, propellants, and the like. The carrier, e.g., non-active ingredient, can be just (sterile) water with the pH adjusted to where the active pharmaceutical agent is very soluble. It is preferred that the pH be at or near 7. Alternatively and preferably, the non-active carrier agent should be physiological saline with the pH adjusted appropriately.

The novel compounds according to the present invention can be administered in any suitable way. The compounds according to the invention can be made up in solid or liquid form, such as tablets, capsules, powders, syrups, elixirs and the like, aerosols, sterile solutions, suspensions or emulsions, and the like. The compounds are advantageously administered via inhalation or insufflation. When the administration form is inhalation or insulation, the compounds are preferably in the form of either an aerosol or a powder.

The term "effective amount" refers to a therapeutically effective amount for treating asthma, chronic obstructive pulmonary disease (COPD), allergic rhinitis, or infectious rhinitis. The terms "therapy" and "therapeutically" encompass all kinds of treatments, including prophylaxis. In particular, "therapeutically effective" means that it is effective for anticholinergic treatment.

For purposes of illustration, dosages are expressed for based on the inhalation of an aerosol solution, such as the product Atrovent Inhalation Aerosol (Boehringer Ingelheim). Adjustments in dosages for administration by other modes of inhaled administration are well known to those skilled in the art.

In general, a therapeutically effective amount of antimuscarinic agent is from about 1 µg to about 1,000 µg, e.g., from about 10 µg to about 1,000 µg or from about 100 µg to about 1000 µg. However, the exact dosage of the specific compound according to the invention will vary depending on its potency, the mode of administration, the age and weight of the patient and the severity of the condition to be treated. The daily dosage may, for example, range from about 0.01 µg to about 10 µg per kg of body weight, administered singly or multiply in doses e.g. from about 1 µg to about 1,000 µg each. The compounds of formula I can be administered from one to four times daily, e.g., once or twice daily.

The dosage form for inhalation can be an aerosol. The minimum amount of an aerosol delivery is about 0.2 ml and the maximum aerosol delivery is about 5 ml. The concentration of the compounds according to the invention may vary as long as the total amount of spray delivered is within the about 0.2 to about 5 ml amount and it delivers a therapeutically effective amount of the compound of formula I. It is well known to those skilled in the art that if the concentration is higher, one gives a smaller dose to deliver the same effective amount.

The dosage form for inhalation can also be via intranasal spray. The minimum amount of an aerosol delivery is about 0.02 ml per nostril and the maximum aerosol delivery is about 0.2 ml per nostril. The concentration of the compounds according to the invention may vary as long as the total amount of spray delivered is within about 0.02 ml per nostril to about 0.2 ml per nostril, e.g., between about 0.05 ml per nostril and about 0.08 ml per nostril, and it delivers a therapeutically effective amount of the compound of formula I.

Aerosols for inhalation of various pharmaceutical agents are well known to those skilled in the art, including many aerosols for treating asthma. Aerosols may be produced with a nebulizer. Typically, the nebulizer is charged with a carrier solution and the compound of formula I in an amount sufficient to effectively deliver a therapeutically effective amount of the antimuscarininc compound. For instance, depending upon the nebulizer and its operating conditions, the nebulizer may be charged with several hundred mg of antimuscarinic compound in order to deliver about 1 µg to about 1000 µg, e.g., from about 10 µg to about 1000 µg or from about 50 µg to about 500 µg, of the compound of formula I.

The dosage form for inhalation may also be in powder form. Powders for inhalation of various pharmaceutical agents are well known to those skilled in the art, including many powders for treating asthma. When the dosage form is a powder, the compounds according to the invention can be administered in pure form or diluted with an inert carrier. When an inert carrier is used, the compounds according to the invention are compounded such that the total amount of powder delivered delivers an "effective amount" of the compounds according to the invention. The actual concentration of the active compound may vary. If the concentration is lower, then more powder must be delivered; if the concentration is higher, less total material must be delivered to provide an effective amount of the active compound according to the invention.

Pharmaceutically acceptable refers to those properties and/or substances which are acceptable to the patient from a pharmacological/toxicological point of view and to the manufacturing pharmaceutical chemist from a physical/chemical point of view regarding composition, formulation, stability, patient acceptance and bioavailability.

EXAMPLES

Without further elaboration, it is believed that one skilled in the art can, using the preceding description, practice the present invention to its fullest extent. The following detailed examples describe how to prepare the various compounds and/or perform the various processes of the invention and are to be construed as merely illustrative, and not limitations of the preceding disclosure in any way whatsoever. Those skilled in the art will promptly recognize appropriate variations from the procedures both as to reactants and as to reaction conditions and techniques.

All temperatures are in degrees Celsius. Ether refers to diethyl ether. Physiological saline refers to a 0.9% aqueous sodium chloride solution. When solvent pairs are used, the ratios of solvents used are volume/volume (v/v). When the solubility of a solid in a solvent is used the ratio of the solid to the solvent is weight/volume (wt/v).

Example I

Production of (2R)-N-[1-(6-aminopyridin-2-ylmethyl)1-methylpiperdin-4-yl]-2-[(1R)-3,3,-difluorocyclopentyl]-2-hydroxy-2-phenylacetamide iodide (2R)-N-[1-(6-aminopyridin-2-ylmethyl)piperdin-4-yl]-2-[(1R)-3,3,-difluorocyclopentyl]-2-hydroxy-2-phenylacetamide (1) is prepared according to the procedures described in U.S. Patent Application No. 2001/0051727A1. To COMPOUND (1), free base in toluene, is added methyl iodide (1 ml). Acetonitrile (5 ml) is added to the mixture and stirred over night at 20–25° C. The solvent is removed by blowing dry nitrogen. Acetone (1 ml) and hexane (2 ml) are added and the mixture is filtered at 20–25° C. to give the title compound. The identity of the compound has been further verified and characterized by NMR analysis, mass spectrometry, and melting point determination.

Example II

Bronchodilatory Effect of Inhaled Quaternary Ammonium Salts in Balb/c Mice

Female BALB/c mice, weight range 19–22 g, are obtained from Charles River Laboratories (Kingston, N.C.). They receive food and water ad libitum. All procedures in these studies are performed in compliance with the Animal Welfare Act P.egulation, 9CFP. Parts 1 and 2, Publication (NIH) 85-23, 1985.

Compounds for aerosol administration are prepared in sterile Dulbecco's Phosphate Buffered Saline. Mice are placed in a carousel-style, nose only, exposure chamber and allowed to inhale aerosols for five minutes, using an ICN SPAG-2 nebulizer. This nebulizer generates a mean aerosol particle size of 1.3 microns at a rate of approximately 0.25 ml/minute.

Ten minutes and 36 hours later, the mice are moved to whole body plethysmograph chambers. Bronchoconstriction is induced in mice by administration of an 80 mg/ml methacholine (MC) aerosol into the plethysmograph chambers for 5 minutes. The mice are allowed to inhale an aerosol containing 80 mg/ml methacholine following inhalation treatment with DPBS vehicle (Dulbecco's Phosphate Buffered Saline), or 80 mg/ml methacholine following inhalation treatment with 1.29 mg/ml of the title compound of example I. The average enhanced pause (Penh, lung resistance), corresponding to airflow resistance, is determined and statistically analyzed using Kruskal-Wallis one way ANOVA. In order to determine the baseline, saline aerosol (without methacholine) is also separately administered to the mice, treated with the compound of example I in an aerosol formulation, 50 μg every 8 hr continuously for dyspnea. After a week of treatment, the $FEV_1$/FVC ratio improves to about 65%.

I claim:

1. A quaternary ammonium compound of formula I

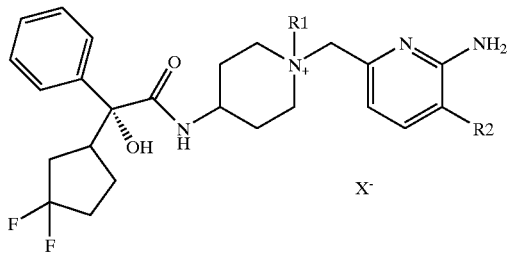

and any stereoisomers thereof, wherein $R_1$ is selected from $C_1$–$C_6$ alkyl, —$CH_2$—($C_1$–$C_4$ alkenyl), and —$CH_2$—($C_1$–$C_6$ alkynyl), each of which is optionally substituted with a group selected from phenyl, $C_1$–$C_4$ alkoxy, and hydroxyl;

$R_2$ is selected from H or OH; and

X represents an anion of a pharmaceutically acceptable acid.

2. The compound of claim 1, wherein X is selected from the group consisting of the anions of the following acids: tartaric, hydrochloric, hydrobromic, hydroiodic, sulfuric, phosphoric, nitric, citric, methanesulfonic, $CH_3$—$(CH_2)_n$—COOH where n is 0–4, HOOC—$(CH_2)_n$—COOH where n is 1–4, HOOC—CH═CH—COOH, and benzoic.

3. The compound of claim 1, wherein X is selected from the group consisting of iodide, bromide, and chloride.

4. The compound of claim 1, wherein X is iodide.

5. The compound of claim 1, wherein X is bromide.

6. The compound of claim 1, wherein X is chloride.

7. The compound of claim 1, wherein $R_1$ is methyl.

8. A compound (2R)-N-[1-(6-aminopyridin-2-ylmethyl) 1-methylpiperdin-4-yl]-2-[(1R)-3,3,-difluorocyclopentyl]-2-hydroxy-2-phenylacetamide iodide.

9. A pharmaceutical composition comprising a pharmaceutical carrier and a therapeutically effective amount of a quaternary ammonium compound of formula I

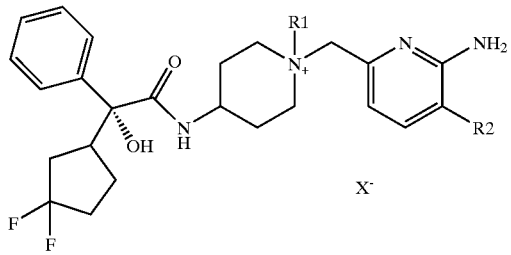

and any stereoisomers thereof, wherein $R_1$ is selected from $C_1$–$C_6$ alkyl, —$CH_2$—($C_1$–$C_4$ alkenyl), and —$CH_2$—($C_1$–$C_6$ alkynyl), each of which is optionally substituted with a group selected from phenyl, $C_1$–$C_4$ alkoxy, and hydroxyl;

$R_2$ is selected from H or OH; and

X represents an anion of a pharmaceutically acceptable acid.

10. The method of treating a mammal for asthma, Chronic Obstructive Pulmonary Disease, allergic rhinitis, and infectious rhinitis, comprising:

administering a therapeutically effective amount of a quaternary ammonium compound of formula I, having the structure

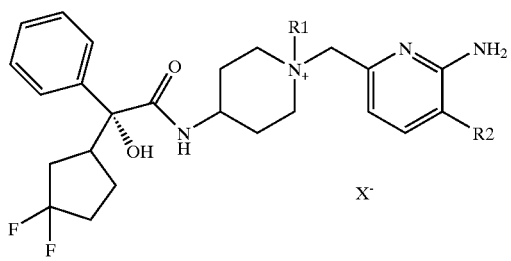

and any stereoisomers thereof, wherein $R_1$ is selected from $C_1$–$C_6$ alkyl, —$CH_2$—($C_1$–$C_4$ alkenyl), and —$CH_2$—($C_1$–$C_6$ alkynyl), each of which is optionally substituted with a group selected from phenyl, $C_1$–$C_4$ alkoxy, and hydroxyl;

$R_2$ is selected from H or OH; and

X represents an anion of a pharmaceutically acceptable acid.

* * * * *